United States Patent [19]  [11]  4,442,208
Tsuchida et al.  [45]  Apr. 10, 1984

[54] METHOD FOR PRODUCING L-ISOLEUCINE BY FERMENTATION

[75] Inventors: Takayasu Tsuchida, Yokohama; Kiyoshi Miwa, Matsudo; Shigeru Nakamori, Yokohama, all of Japan

[73] Assignee: Ajinomoto Co., Inc., Tokyo, Japan

[21] Appl. No.: 392,145

[22] Filed: Jun. 25, 1982

[30] Foreign Application Priority Data

Jun. 25, 1981 [JP] Japan ................................. 56-98699

[51] Int. Cl.³ ..................... C12P 13/06; C12N 15/00; C12N 1/20
[52] U.S. Cl. .................................. 435/116; 435/172; 435/253
[58] Field of Search ........................ 435/172, 116, 253

[56] References Cited

U.S. PATENT DOCUMENTS 4,237,228 12/1980 Zhdanova et al. ................... 435/116
4,329,427 5/1982 Updike et al. ....................... 435/116
4,346,170 8/1982 Sano et al. ........................... 435/172
4,347,318 8/1982 Miwa et al. ......................... 435/172

Primary Examiner—Alvin E. Tanenholtz
Attorney, Agent, or Firm—Oblon, Fisher, Spivak, McClelland & Maier

[57] ABSTRACT

L-isoleucine is produced by a fermentation process comprising aerobically culturing in an aqueous culture medium an L-isoleucine producing microorganism obtained by isolating a transformed strain resistant to $\alpha$-amino-$\beta$-hydroxy valeric acid prepared by incorporating into a recipient strain of the genus Brevibacterium orCorynebacterium, which is sensitive to $\alpha$-amino-$\beta$-hydroxy valeric acid, a plasmid DNA obtained from a microorganism of the genus Brevibacterium or Corynebacterium into which has been inserted a fragment of chromosomal DNA derived from a DNA-donor strain of the genus Brevibacterium or Corynebacterium which is resistant to $\alpha$-amino-$\beta$-hydroxy valeric acid; and recovering L-isoleucine which accumulates in the resulting culture liquid.

5 Claims, No Drawings

METHOD FOR PRODUCING L-ISOLEUCINE BY FERMENTATION

BACKGROUND OF THE INVENTION

1. Field of the Invention

The present invention relates to a method for producing L-isoleucine by fermentation, and particularly to a method for producing L-isoleucine with a microorganism of the genus Brevibacterium and Corynebacterium constructed by a gene splicing technique.

2. Description of the Prior Art

In the past, in order to render a wild strain capable of producing L-isoleucine from carbohydrates, it has been necessary to induce artificial mutants from the wild strain. In this regard there are many known L-isoleucine producing artificial mutants.

Examples of known isoleucine producing microorganisms include mutants of Serratia resistant to isoleucine-hydroxamate (Japanese Published Examined Patent Application No. 30593/1977), mutants of Corynebacterium glutamicum requiring L-leucine for growth (Japanese Published Examined Patent Application No. 38995/1972), mutants of Brevibacterium and Corynebacterium resistant to $\alpha$-amino-$\beta$-hydroxy valeric acid (hereinafter referred to as AHV), (Japanese Published Examined Patent Application No. 2880/1967), mutants of Brevibacterium resistant to AHV and requiring lysine for growth (Japanese Published Examined Patent Application No. 6237/1976), mutants of Brevibacterium resistant to AHV and O-methylthreonine (Japanese Published Examined Patent Application No. 21077/1976), mutants of Corynebacterium resistant to S-(2-aminoethyl)-cysteine (Japanese Published Unexamined Patent Application No. 61290/1977), mutants of Escherichia resistant to 2-amino-3-methyl thiobutyric acid (Japanese Published Unexamined Patent Application No. 69881/1978) and mutants of Brevibacterium resistant to AHV and trichloroalanine (Japanese Published Unexamined Patent Application No. 35287/1979).

Another approach to increase the productivity of amino acids in microorganisms is found in U.S. Pat. No. 4,278,765 and in Japanese Published Unexamined Patent Application Nos. 131397/1980, 1890/1981, 18596/1981, 82095/1981, 85287/1981, 117795/1981, 144092/1981 and 144093/1981. In this technique Escherichia coli stains transformed with a recombinant plasmid DNA and constructed by a gene splicing technique to produce various kinds of amino acids are disclosed.

However, it has been difficult to construct a commercially useful isoleucine producer of Escherichia coli by the gene splicing technique, because original Escherichia strains do not express high productivity for L-isoleucine and recombinant strains derived from such Escherichia strains do not product high amounts of L-isoleucine.

On the other hand, there are many strains in the genera of Brevibacterium and Corynebacterium which produce large amounts of L-isoleucine, and for this reason there may be strains of Corynebacterium and Brevibacterium which are suitable as original strains for the construction of L-isoleucine producers by the gene splicing technique. However, although the presence of plasmids in the strains of Brevibacterium and Corynebacterium are known (Publication of European Patent Application No. 0030391), the plasmids have no specific characteristics which would be useful as a marker for the identification of the plasmids. Therefore, it has been very difficult to select recombinant plasmids, derived from the plasmids of Brevibacterium and Corynebacterium. For the reason noted above, it has been difficult to construct an L-isoleucine producer from L-isoleucine producing Brevibacterium and Corynebacterium by the gene splicing technique.

A need, therefore, continues to exist for the development of a process for production of L-isoleucine in high yields.

SUMMARY OF THE INVENTION

Accordingly, one object of the present invention is to provide a method for producing L-isoleucine by fermentation in high yields.

Briefly, this object and other objects of the present invention, as hereinafter will become more readily apparent, can be attained in a method for producing L-isoleucine by fermentation which comprises aerobically culturing in an aqueous culture medium an L-isoleucine producing microorganism obtained by isolating a transformed strain resistant to AHV prepared by incorporating into a recipient strain of the genus Brevibacterium or Corynebacterium which is sensitive to AHV, a plasmid DNA obtained from a microorganism of the genus Brevibacterium or Corynebacterium into which has been inserted a fragment of chromosomal DNA derived from a DNA-donor strain of the genus Brevibacterium or Corynebacterium which is resistant to AHV, and recovering L-isoleucine which accumulates in the resulting culture liquid.

The present invention also provides a method for constructing an L-isoleucine producing strain by (a) separating a plasmid DNA from a microorganism of the genus Brevibacterium or Corynebacterium, (b) inserting into the plasmid DNA a fragment of chromosomal DNA derived from a DNA-donor strain of the genus Brevibacterium or Corynebacterium resistant to AHV to obtain a recombinant plasmid DNA, (c) incorporating the recombinant plasmid DNA into a recipient strain of the genus Brevibacterium or Corynebacterium which is sensitive to AHV, and (d) isolating a transformed strain resistant to AHV.

DETAILED DESCRIPTION OF THE PREFERRED EMBODIMENTS

The central feature of the present invention is that it has now been found that L-isoleucine producing strains of the genus Brevibacterium or Corynebacterium can be obtained by the selection of transformed strains which are resistant to AHV.

The DNA-donor strain used to construct the L-isoleucine producer of this invention is a mutant of the genus Brevibacterium or Corynebacterium resistant to AHV. Strains having a greater L-isoleucine producing capability are used preferably as the DNA-donor. A mutant resistant to AHV used as the DNA-donor can be obtained by conventional mutation techniques such as by exposing the parent strain to 250 $\mu$g/ml of N-methyl-N'-nitro-N-nitrosoguanidine in a buffer solution and separating the colonies which appear on the agar medium containing an amount of AHV sufficient to inhibit the growth of the parent strain. Such a DNA-donor naturally has a chromosomal DNA region which expresses AHV resistance. Preferred DNA-donor strains are resistant to an amount of AHV of more than 100 $\mu$g/ml.

Besides the DNA-donors listed above, AHV-resistant and isoleucine producing strains can be obtained by imparting AHV-resistance by a conventional technique to so-called "Coryneform glutamic acid producing bacteria," of which typical strains are shown below:

Brevibacterium divaricatum ATCC 14020
Brevibacterium saccharoliticum ATCC 14066
Brevibacterium immariophilum ATCC 14068
Brevibacterium lactofermentum ATCC 13869
Brevibacterium roseum ATCC 13825
Brevibacterium flavum ATCC 13826
Brevibacterium thiogenitalis ATCC 19240
Corynebacterium acetoacidophilum ATCC 13870
Corynebacterium acetoglutamicum ATCC 15806
Corynebacterium callunae ATCC 15991
Corynebacterium glutamicum ATCC 13032
Corynebacterium lilium ATCC 15990
Corynebacterium melassecola ATCC 17965

As the vector DNA, plasmids obtained from the Coryneform glutamic acid producing bacteria of the genera Brevibacterium and Corynebacterium or their mutants, and derivatives of the plasmids can be used. Suitable examples of such plasmids include pAM 286, pAM 330, and pHM 1519.

The DNA-recipient used in the present invention includes strains which are sensitive to AHV and which belong to the Coryneform glutamic acid producing bacteria of the genera Brevibacterium and Corynebacterium. When a mutant sensitive to AHV which requires L-isoleucine is used as the DNA-recipient, it is especially more convenient to distinguish the isoleucine producing transformant from the recipient, although the isoleucine producing transformant can be distinguished from the recipient by AHV-resistance.

Chromosomal DNA is extracted from the DNA donor by a well-known technique and treated with a restriction endonuclease by a well-known method (*Biochem. Biophys. Acta* 383:457 (1975)).

The vector DNA is also treated with a restriction endonuclease in an analogous manner. Various kinds of restriction endonucleases can be used, if partial digestion of the chromosomal DNA is to be done. Thereafter, the digested chromosomal DNA and vector DNA are subjected to a ligation reaction.

Recombination of DNA to prepare the recombinant plasmid can be conducted by the ligation reaction with a ligase, or by incorporating deoxyadenylic acid and thymidylic acid, or deoxyguanylic acid and deoxycytidylic acid with terminal transferase into the chromosomal DNA fragment and cleaved vector DNA and by subjecting the modified chromosomal DNA fragment and cleaved DNA to an annealing reaction.

The recombinant DNA thus obtained can be incorporated into the DNA-recipient by treating the cell of the DNA-recipient with calcium chloride to increase its permeability as is reported regarding *E. coli* K-12 (Mandel, M. and Higa, A., *J. Mol. Biol.*, 53, 159 (1970)), or by applying for the incorporation of cells of the DNA-recipient at a specific stage of growth when the cells become capable of having plasmids incorporated therein (competent cell) as is reported for *Bacillus subtilis* (Duncan, C. H., Wilson, G. A. and Young, F. E., *Gene* 1, 153 (1977)). The recombinant DNA can also be incorporated into the DNA-recipient by forming protoplasts or spheroplasts of the DNA-recipient which forms of the cells easily incorporate plasmid DNA therein as is known for *Bacillus subtilis*, Actinomycetes and yeast (Chang, S. and Choen, S. N., *Molec. Gen. Genet.*, 168, 111 (1979)); Bibb, M. J., Ward, J. M. and Hopwood, O. A., *Nature*, 274, 398 (1978); Hinnen, A., Hicks, J. B. and Fink, G. R., *Proc. Natl. Acad. Sci., USA*, 75, 1929 (1978)).

The desired transformant can be obtained by isolating the colonies which appear on a medium containing an amount of AHV which inhibits the growth of the DNA-recipient. Isoleucine producers can be obtained from the isolated colonies in high frequency.

The methods of culturing the L-isoleucine producing strains thus obtained are conventional, and are similar to the methods for the cultivation of known L-isoleucine producing microorganisms. The culture medium employed can be a conventional medium containing carbon sources, nitrogen sources, inorganic ions and, when required, minor organic nutrients such as vitamins and amino acids. Examples of suitable carbon sources include glucose, sucrose, lactose, starch hydrolysate and molasses. Gaseous ammonia, aqueous ammonia and ammonium salts and other nitrogen containing materials can be used as the nitrogen source.

Cultivation of the recombinant microorganisms is conducted under aerobic conditions in which the pH and the temperature of the medium are adjusted to a suitable level and continued until the formation of L-isoleucine ceases.

The L-isoleucine which accumulates in the culture medium can be recovered by conventional procedures.

By the method of the present invention, L-isoleucine can be produced in higher yields than has been achieved in previously known methods using artificial mutants of Brevibacterium and Corynebacterium.

Having generally described this invention, a further understanding can be obtained by reference to certain specific examples which are provided herein for purposes of illustration only and are not intended to be limiting unless otherwise specified.

EXAMPLE 1

(1) Extraction of chromosomal DNA

*Corynebacterium glutamicum* AJ 11560 (FERM-P 5485) was exposed to 250 μg/ml N-methyl-N'-nitro-N-nitrosoguanidine in 1/10 M phosphate buffer of pH 7.2 at 30° C. for 30 minutes and colonies which appeared on a minimum medium (M medium) (containing, per liter, 20 g glucose, 10 g ammonium sulfate, 2.5 g urea, 1 g $KH_2P_4$, 0.4 g $MgSO_4.7H_2O$, 50 μg biotin, 200 μg thiamine.HCl, 0.01 g $FeSO_4$, 0.01 g $MnSO_4.4H_2O$, 1 g AHV and 2 g agar (pH 7.0)) were isolated as the AHV-resistant strains.

One of the AHV-resistant strains, No. 11 (NRRL B-15086) was cultured at 30° C. for 3 hours with shaking in 1 l of CMG-medium containing 1 g/dl peptone, 1 g/dl yeast extract, 0.5 g/dl glucose and 0.5 g/dl NaCl (pH was adjusted to 7.2), and bacterial cells in the exponential growth phase were harvested. Chromosomal DNA was extracted by a conventional phenol-method, and 0.8 mg of purified DNA was obtained.

*Corynebacterium glutamicum* AJ 11560 was newly isolated as a strain suitable for the purposes of the present invention. This strain was classified in section III of the genus *Corynebacterium* described in *Bergey's Manual of Determinative Bacteriology* (8th edition, 1974). However, the taxonomic characteristics of the species belonging to section III are not disclosed in the Manual. Rather, section III of the Manual only discloses the name of species of bacteria. Therefore, all original reports disclosed in the Manual as to section III are referred to. AJ 11560 was identified with *Corynebacterium glutamicum* described in *Bull. Agr. Chem. Soc. Japan*, 22, 176–185 (1958) and *J. Gen. Appl. Microbiol.*, 13, 279–301 (1967).

(2) Preparation of vector DNA

As a vector, the DNA of pAM 286, a plasmid of *Corynebacterium glutamicum* was prepared as follows:

*Corynebacterium glutamicum* AJ 11560 harboring the plasmid pAM 286 was incubated at 30° C. in 1 l of CMG medium until the late log phase. The cells were harvested and then lysed by treatment with lysozyme and SDS. The lysate was centrifuged at 30,000 ×g for 30 minutes to obtain the supernatant. After concentrating the supernatant, 60 μg of pAM 286 plasmid DNA was obtained by fractionation using agarose gel electrophoresis.

(3) Insertion of chromosomal DNA fragment into vector

A 10 μg amount of the chromosomal DNA was treated with the restriction endonuclease BclI at 37° C. for 10, 30 and 60 minutes, respectively, to cleave the DNA chains, and then heated at 65° C. for 5 minutes, respectively. Five μg of the vector DNA was also treated with the restriction endonuclease XbaI at 37° C. for 60 minutes to cleave the DNA completely, and then heated at 65° C. for 5 minutes.

The digested chromosomal DNA solution and cleaved vector DNA solution were mixed and subjected to a ligation reaction of DNA fragments by a T4 phage DNA-ligase in the presence of ATP and dithiothreitol at 10° C. for 24 hours. The reaction mixture was then heated at 65° C. for 5 minutes, and a two fold volume of ethanol was added to it. The precipitated recombinant DNA was recovered.

(4) Genetic transformation with recombinant plasmid

An isoleucine requiring strain, No. 144 (NRRL B-15088) which was derived from Corynebacterium glutamicum AJ 11560 by N-methyl-N'-nitro-N-nitrosoguanidine mutagenesis, (250 μg/ml in a 1/10 M phosphate buffer, pH 6.0 at 30° C. for 60 minutes, and isolated as the isoleucine requiring mutant) was cultured in 20 ml of CMG medium at 30° C. with shaking until the cell density reached 0.6 A 650/ml. Cells were harvested, suspended in ice-cooled 0.1 M MgCl$_2$, collected, suspended in 5 ml of 0.1 M CaCl$_2$, with ice-cooling, and held at 0° C. for 20 minutes with occasional shaking. The cells were separated from the suspension and suspended again in a small amount of 0.1 M CaCl$_2$, thereby obtaining a suspension of competent cells. Into the competent cell suspension was added the solution of DNA obtained in step (3) to introduce the DNA into the cell. The reaction mixture was spread onto the plate of an M-medium.

Colonies appeared on the plate after incubation at 37° C. for 4 days and the transformed cells which were AHV-resistant were picked up and L-isoleucine producing transformants were selected.

Thus, AJ 11686 (FERM-P 6011=FERM-BP 135) was obtained as the best isoleucine producing transformant.

(5) Producton of L-isoleucine

The L-isoleucine productivity of AJ 11686 obtained in step (4) was tested in comparison to the DNA-donor and DNA-recipient. The results are shown in Table 1.

The fermentation medium contained 10 g./dl glucose, 3 g/dl ammonium sulfate, 0.1 g KH$_2$PO$_4$, 0.04 g/dl MgSO$_4$.7H$_2$O, 2 mg/dl soyprotein hydrolysate ("MIEKI"), 10 μg/dl thiamine HCl, 50 μg/dl biotin, 1 mg/dl FeSO$_4$.7H$_2$O, 1 mg/dl MnSO$_4$.4H$_2$O and 5 g/dl CaCO$_3$ (separately sterilized) and the pH was adjusted to 7.2.

Twenty ml batches of the fermentation medium were placed in 500 ml flasks, inoculated with one loopful inoculum of the test microorganism, and cultivated at 31° C. for 72 hours.

The amount of L-isoleucine in the supernatant of the fermentation broth was determined by microbiological assay.

TABLE 1

| Microorganism tested | L-isoleucine produced (mg/dl) |
|---|---|
| No. 11 | 60 |
| No. 144 | 0 |
| AJ 11686 | 120 |

EXAMPLE 2

(1) Extraction of chromosomal DNA

In a manner consistent with procedure described in step (1) of Example 1, 2.4 mg of chromosomal DNA was obtained from a AHV resistant mutant, No. 18 (NRRL B-15087) which had been derived from *Brevibacterium lactofermentum* ATCC 13869.

(2) Preparation of vector DNA

In the method shown in step (2) of Example 1, 150 μg of a plasmid pAM 330 (3×10$^6$ dalton) was separated from *Brevibacterium lactofermentum* ATCC 13869 as the vector DNA.

(3) Insertion of chromosomal DNA fragment into vector

Ten μg of chromosomal DNA obtained in step (1) was digested by the manner shown in step (3) of Example 1. The vector DNA was also cut by the manner shown in step (3), and the digested chromosomal DNA and the cut vector DNA were subjected to the ligation reaction shown in step (3) of Example 1.

(4) Genetic transformation with the recombinant plasmid

From *Brevibacterium lactofermentum* ATCC 13869. No. 146 (NRRL B-15089) which requires L-isoleucine was induced as the DNA-recipient by the method shown in step (4) of Example 1, A transformant, AJ 11687 (FERM-P 6010=FERM-BP 134) resistant to AHV and capable of producing L-isoleucine was obtained using the DNA-recipient.

(5) Production of L-threonine

The transformant AJ 11687 obtained in step (4) was tested for its ability to produce L-threonine by the method of step (5) of Example 1. The results are shown in Table 2.

TABLE 1

| Microorganism tested | L-threonine produced (mg/dl) |
| --- | --- |
| No. 18 | 82 |
| No. 146 | 0 |
| AJ 11687 | 145 |

Having now fully described the invention, it will be apparent to one of ordinary skill in the art that many changes and modifications can be made thereto without departing from the spirit or scope of the invention as set forth herein.

What is claimed as new and desired to be secured by Letters Patent of the United States is:

1. A method of producing L-isoleucine by fermentation, which comprises:
   aerobically culturing in an aqueous culture medium an L-isoleucine producing microorganism selected from the group consisting of *Corynebacterium glutamicum* AJ 11686 and *Brevibacterium lactofermentum* AJ 11687.
2. The method of claim 1, wherein said microorganism is *Corynebacterium glutamicum* AJ 11686.
3. The method of claim 1, wherein said microorganism is *Brevibacterium lactofermentum* AJ 11687.
4. *Corynebacterium glutamicum* AJ 11686.
5. Brevibacterium lactofermentum AJ 11687.